United States Patent [19]

Weber

[11] Patent Number: 5,147,315
[45] Date of Patent: Sep. 15, 1992

[54] ACCESS CATHETER AND SYSTEM FOR USE IN THE FEMALE REPRODUCTIVE SYSTEM

[75] Inventor: Mark V. Weber, Goffstown, N.H.

[73] Assignee: C. R. Bard, Inc., Murray Hill, N.J.

[21] Appl. No.: 505,426

[22] Filed: Apr. 6, 1990

[51] Int. Cl.⁵ .......................................... A61M 5/178
[52] U.S. Cl. ................................ 604/164; 604/282; 604/906; 606/119; 600/35
[58] Field of Search .................. 604/55, 280, 282, 906, 604/117, 164; 600/33-35; 606/119

[56] References Cited

U.S. PATENT DOCUMENTS

| | | | |
|---|---|---|---|
| 3,380,453 | 4/1968 | Leville | 604/906 |
| 3,416,531 | 12/1968 | Edwards | 604/282 |
| 3,618,613 | 11/1971 | Schulte . | |
| 4,425,919 | 1/1984 | Alston, Jr. et al. | 604/282 |
| 4,597,755 | 7/1986 | Samson et al. | 604/96 |
| 4,601,698 | 7/1986 | Moulding, Jr. | 604/55 |
| 4,654,025 | 3/1987 | Cassou et al. | 604/55 |
| 4,700,701 | 10/1987 | Montaldi | 604/55 |
| 4,737,153 | 4/1988 | Shimamura et al. | 604/282 |
| 4,756,708 | 7/1988 | Martin | 604/282 |
| 4,832,681 | 5/1989 | Lenck | 604/282 |
| 4,846,785 | 7/1989 | Cassou et al. | 604/55 |
| 4,863,423 | 9/1989 | Wallace | 604/280 |
| 4,865,589 | 9/1989 | Simmet et al. | 604/96 |
| 4,905,667 | 3/1990 | Foerster et al. | 604/280 |
| 4,922,924 | 5/1990 | Gambale et al. | 604/280 |

FOREIGN PATENT DOCUMENTS

| | | | |
|---|---|---|---|
| 6617799 | 6/1967 | Netherlands | 604/55 |
| 2070437 | 9/1981 | United Kingdom | 604/55 |
| 2206118 | 12/1988 | United Kingdom | 604/280 |

OTHER PUBLICATIONS

Gardner, "Chemical Synonyms and Tradenames", Eighth Edition, ©1978 by The Technical Press, Ltd., p. 673.

Jansen et al., "Cathertisation of the Fallopian Tubes from the Vagina" The Lancet, No. 8554, vol. II for 1987, Aug. 8, 1987, pp. 309-310.

Jansen et al., "Nonoperative Embryo Transfer to the Fallopian Tube", New England Journal of Medicine, pp. 288-291, Aug. 4, 1988.

USCI Catalog, "Profile Plus Balloon Dilatation Catheter", p. 9, 1988.

USCI Catalog, "Radiology Steerable Guide Wires", p. 35, 1988.

*Primary Examiner*—C. Fred Rosenbaum
*Assistant Examiner*—Straight, Jr., Ronald
*Attorney, Agent, or Firm*—Wolf, Greenfield & Sacks

[57] ABSTRACT

A catheter for accessing a body cavity such as the reproductive system of the female, the catheter including a shaft which is connected at its distal end to a nonexpansible segment. A lumen in the shaft communicates with a passage in the segment. The segment further includes reinforcing material disposed within the segment to resist constriction of the passage. A catheter system and methods of using same includes such an access catheter and an introducing catheter through which the access catheter is insertable, and a transfer catheter which is insertable through the access catheter. The invention is useful particularly in treatment of infertility by placing reproductive cells in the uterus or a fallopian tube.

15 Claims, 2 Drawing Sheets

ACCESS CATHETER AND SYSTEM FOR USE IN THE FEMALE REPRODUCTIVE SYSTEM

FIELD OF THE INVENTION

This invention relates to catheter systems for artificial insemination.

BACKGROUND OF THE INVENTION

A number of techniques are used to perform artificial insemination. Typically, gametes or zygotes are introduced via a catheter into the uterus or a fallopian tube. The medical community is not in complete agreement as to the best location for placement of gametes or zygotes. There is controversy whether uterine or fallopian tube placement is better and, with respect to each, as to the precise location within the uterus or fallopian tube.

One transcervical procedure described by R. Jansen in "Catheterisation of the Fallopian Tubes from the Vagina", The Lancet, Aug. 8, 1987, page 309, utilizes a catheterization system that is inserted through the vagina and cervix, through the uterus and into the fallopian tube to place reproductive cells in the fallopian tube. The system includes an introducing catheter, an obturator, and a transfer catheter. The obturator is used to straighten and stiffen the introducing catheter during insertion. The introducing catheter, stiffened by the obturator, is advanced into the vagina and through the cervix. The distal portion of the introducing catheter is normally curved to assist positioning of the tip at the entrance of the fallopian tube when the introducing catheter is disposed in the uterus. After the distal portion of the introducing catheter is within the uterus, the obturator is withdrawn and the introducing catheter assumes its curved shape. It is manipulated to locate the tip at the entrance to the fallopian tube.

Reproductive cells are loaded into the distal end of the transfer catheter, and the transfer catheter then is passed through the introducing catheter and is advanced into the fallopian tube to a desired position. The cells then are expelled from the transfer catheter by flushing the catheter with a liquid, such as a culture medium, e.g., Hams Solution. Preloading the transfer catheter at its distal end avoids dilution of the reproductive cells which would occur if the cells were delivered through the proximal end of the transfer catheter using a large quantity of flushing fluid.

The foregoing procedure relies on the transfer catheter to force its way through the fallopian tube until the desired position is reached. Much of the fallopian tube normally is in a collapsed condition, however, and manipulation of the loaded transfer catheter within the fallopian tube can cause premature spillage of some of the reproductive cells before the transfer catheter can be advanced fully to the desired position within the fallopian tube. Also, the musculature of the fallopian tube can crush the transfer catheter which may prevent its advance or cause additional spillage of reproductive cells.

Another procedure, as disclosed in U.S. Pat. No. 4,832,681 (Lenck), utilizes a surgical method of installing a catheter through the uterine wall to implant an ovum or zygote in the uterine cavity. The catheter is made of a flexible tube such as silicone elastomer reinforced with a coiled wire. The distal end of the tubing is installed through the uterine wall by advancing it through the vagina, making an incision in the upper portion of the vagina, and advancing the tubing along the outside of the uterus. An incision is made in the uterine wall and the distal end of the tubing then is inserted through the uterine incision to communicate with the uterine cavity. The tubing is relatively large (having an inner diameter of between 2 and 2.5 mm and an outer diameter of between 4 and 4.5 mm) and is unsuitable for insertion within the fallopian tube. The technique of installing the tubing involves the attendant risks and trauma of surgery.

It would be desirable to provide an artificial insemination system usable for both fallopian tube and uterine placement of reproductive cells. Additionally, it would be desirable to provide such a system in which the precise location where the reproductive cells are deposited can be determined. Information as to the actual placement of reproductive cells at varying depths and locations within the reproductive system of the patient may be of importance in connection with subsequent placement of reproductive cells in that patient. It is among the general objects of the invention to provide such a system.

SUMMARY OF THE INVENTION

The present invention utilizes an access catheter having a single lumen shaft and a reinforced, crush-proof segment at the distal end of the shaft. The reinforcement resists constriction of the distal segment by the fallopian tube. The access catheter is very flexible yet it is strong and has a relatively thin wall and large lumen.

The distal segment of the catheter may be formed from inner and outer tubular layers of material with a reinforcement sandwiched between the layers. In one construction, the reinforcement comprises a helical coil formed from rectangular cross section wire. The shaft may be formed by a single extruded tube to which the distal segment is joined. The distal segment has a smaller outer diameter than that of the shaft, preferably less than 0.08 inch and most preferably less than 0.045 inch when it is desired to advance the access catheter into the fallopian tube. It is also preferable for the segment to have an inner diameter of at least 0.028 inch, and more preferably at least 0.030 inch. The small outer diameter and thin wall of the distal segment results in a flexible yet strong distal segment which is readily insertable into a fallopian tube.

It is desirable for the reinforcing material to be visible to monitoring radiation such as ultrasound. The proximal end of the shaft of the access catheter may include at least one visually perceptible marker for visual alignment relative to the reproductive system or relative to an introducing catheter in which the access catheter is insertable.

This invention further features a catheter system and method involving the access catheter, an introducing catheter, and a transfer catheter. The system may further include use of an obturator and a flexible guide for assisting insertion of the introducing catheter and the access catheter, respectively. One or more of the components may include visually perceptible markers enabling alignment and relative measurement of the position of the components with respect to themselves or with respect to the patient's reproductive system.

It is among the objects of the invention to provide a novel access catheter which may be used in combination with an introducing catheter and a transfer catheter for delivering materials to a body cavity.

It is a further object of the invention to provide an access catheter having a distal segment which can have both high flexibility and high hoop strength to resist collapsing of the distal segment.

A still further object of the invention is to provide such an access catheter which can have a very thin wall to provide a large inner diameter and a relatively small outer diameter.

A still further object of the invention is to provide an improved catheter system and method for accurately placing materials within a female reproductive system.

A further object of the invention is to provide such a catheter system for placing gametes or zygotes transcervically into the uterus or a fallopian tube.

Yet another object of the invention is to provide methods of using such catheters and of aligning markers on the components relative to each other and relative to the reproductive system to accurately place the reproductive material.

DESCRIPTION OF THE DRAWINGS

The foregoing and other objects and advantages of the invention will be appreciated more fully from the following further description thereof with reference to the accompanying drawings wherein.

DESCRIPTION OF THE ILLUSTRATIVE EMBODIMENT

Figure 2:
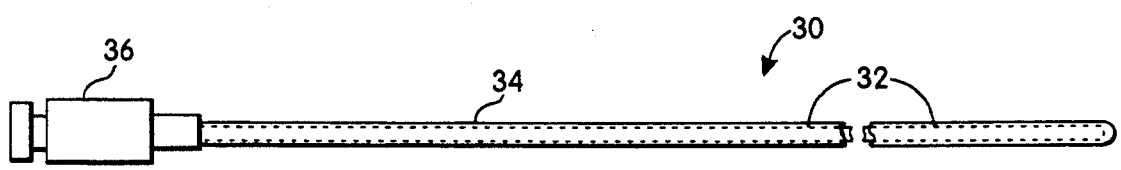
FIG. 2 is a diagramatic view of an obturator insertable within the introducing catheter of FIG. 1.
Figure 3:
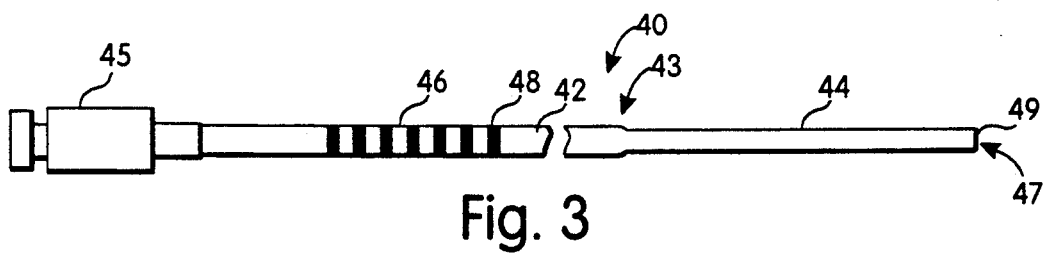
FIG. 3 is a diagramatic view of an access catheter according to the invention.
Figure 4:
FIG. 4 is a diagramatic view of a transfer catheter insertable through the access catheter.
Figure 5:
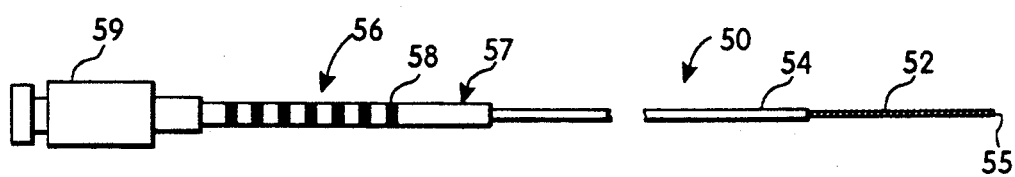
FIG. 5 is a schematic view of a guide according to the invention for assisting placement of the access catheter.

FIGS. 1–4 illustrate the elements of the catheter system of the present invention including an introducer catheter 10 (FIG. 1), an obturator 30 (FIG. 2), an access catheter 40 (FIG. 3) and a transfer catheter 60 (FIG. 4). The catheter system may further include a guide 50 (FIG. 5). Each of the foregoing elements may be considered as having a proximal end (to the left in the drawings) and a distal end (to the right in the drawings), the distal end being inserted into the patient and the proximal end remaining outside of the patient and controllable by the physician. FIGS. 1–5 are arranged to suggest schematically the relative lengths of the introducer catheter 10, obturator 30, access catheter 40, transfer catheter 60, and guide 50.

Figure 6:
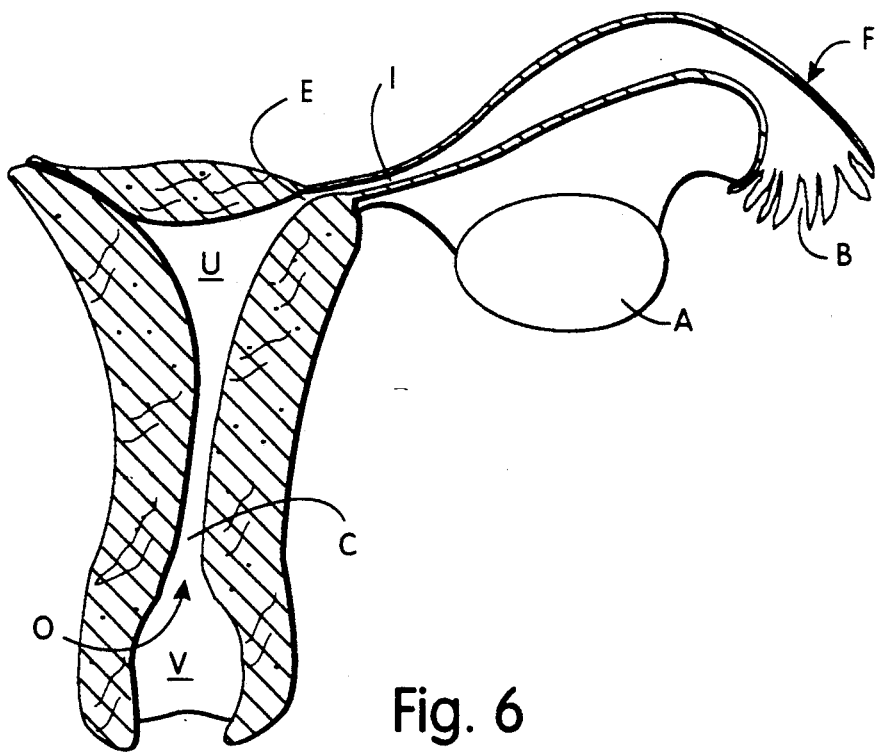
FIG. 6 is a schematic representation of a portion of a female reproductive system.

The foregoing system is intended for use in placing gametes or zygotes selectively at a predetermined location in the fallopian tube or the uterus nonsurgically and with vaginal access. FIG. 6 illustrates diagramatically a portion of the human female reproductive system, including a vagina V, a cervix C, a uterus U, a fallopian tube F, and an ovary A. It is considered desirable by many in the medical community for artificial insemination to simulate natural conception as closely as possible. During natural conception, an egg is released from an ovary A and travels into the fallopian tube F through finger like fimbria B. The egg then travels down the fallopian tube, through narrowed isthmus I and past entrance E into the uterus U. There is some uncertainty as to the actual location at which sperm, traveling through the cervix C and into the uterus U and into the fallopian tube F, unite with the egg. The catheter system according to the invention enables accurate placement of reproductive cells at a wide range of locations within the uterus U and the fallopian tube F.

One of the difficulties of depositing reproductive cells in the fallopian tube F is that the tube F normally is in a collapsed condition. The catheter therefore must be forced through the collapsed fallopian tube F, establishing a sufficient passage as it is advanced while minimizing trauma to the fallopian tube F. Moreover, the most difficult portion of the fallopian tube F to traverse is the narrow-diameter isthmus I beyond the entrance E. Additionally, crushing of the catheter due to the musculature of the fallopian tube must be successfully overcome.

Briefly, the catheter system of the present invention overcomes the foregoing difficulties by an access catheter 40 having a reinforced distal tip 44 which is readily insertable through the entrance E and the isthmus I of a fallopian tube F. The catheter system may be provided as a kit including the access catheter 40, the introducing catheter 10, and the transfer catheter 60. Additionally, the system and kit may include an obturator 30 and a guide 50.

In general, the catheter system is used as follows for accessing a fallopian tube. The obturator 30 is inserted through the proximal end of the introducing catheter 10 to stiffen it.[1] With the rigidity provided by the obturator 30, the introducing catheter 10 is inserted into the vagina V, through the opening 0 of the cervix C, and into the uterus U. The obturator 30 is removed from the introducing catheter 10, and the introducing catheter 10 resumes its curved shape to place the distal tip 14 at the entrance E to the fallopian tube F. The obturator 30 then is withdrawn and the access catheter 40 is advanced through the introducing catheter 10.

[1] The distal 6 cm. of the obturator is malleable and can be formed by hand to any curve desired by the doctor.

Advancement of the access catheter 40 may be assisted using guide 50 which is inserted through the access catheter 40. The combination of the guide 50 and the access catheter 40 is more rigid (has greater column strength) than the access catheter 40 by itself. Therefore, the pushability of the access catheter 40 is enhanced by the guide 50 which is useful for traversing the isthmus I of the fallopian tube F. Also, the flexible spring tip 52 of the guide 50 can be inserted first through the entrance E and isthmus I of the fallopian tube F, after which the access catheter 40 is advanced to "track" the path of the guide 50.

After the access catheter 40 is positioned within the fallopian tube F, the guide 50 is withdrawn and the transfer catheter 60 is inserted through the access catheter 40. Typically, the distal end 66 of the transfer catheter 60 is advanced approximately one cm beyond the distal end 49 of the access catheter 40. A syringe then is mated with the luer 64 of the transfer catheter 60, and the reproductive cells at the distal end of the transfer catheter 60 are discharged at the desired location. Details of the construction and use of the illustrative embodiment are as follows.

Figure 1:
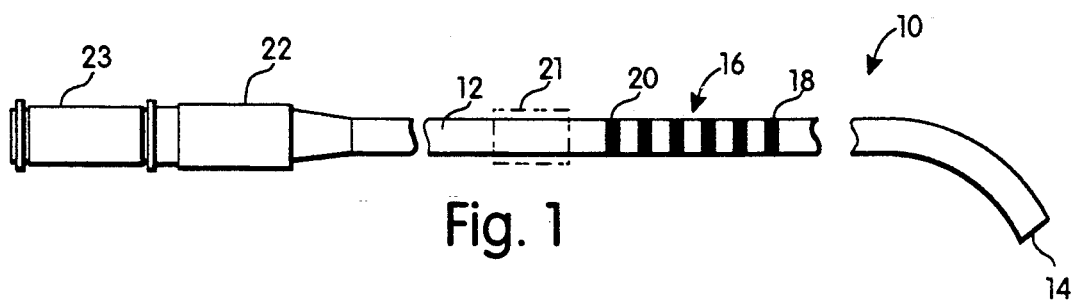
FIG. 1 is a diagramatic illustration of an introducing catheter comprising a portion of the catheter system according to the invention.

The introducing catheter 10, FIG. 1, is a single lumen catheter formed of an inner Teflon lining, a wire reinforcing braid, an outer urethane sleeve, and having an outer diameter of 0.104 inch (2.62 mm) and an inner diameter of 0.072 inch (1.83 mm). In one manufacturing procedure, the introducing catheter 10 is formed by placing a Teflon tube, having an inner diameter of 0.072 inch and a wall thickness of 0.0025 inch, over a mandrel having an outer diameter of approximately 0.070 inch. The Teflon tube is mechanically roughened, and then heated to shrink it onto the mandrel. The ends of the tube are sealed. The assembly then is placed in a chemical bath such as Tetra-etch available from W. L. Gore & Associates, Newark, N.J. to strip fluorine atoms from the polymer. The assembly is removed from the bath, and oxygen and nitrogen in the air interacts with the fluorine depleted carbon atoms to render the surface more compatible to an adhesive which assists in securing the wire braid to the roughened, chemically treated surface. Wire having a diameter of 0.003 inch then is wrapped about the assembly to form the braid, and all but the distal three to six cm of the assembly are coated with a thin layer of epoxy, such as FDA #2 available from Tra-Com, Inc., Medford, Mass. to secure the braid in place. The epoxy then is cured, and the ends of the braid are trimmed, leaving approximately three to six cm of the distal tip without braid or epoxy to provide increased flexibility. The assembly then is placed inside a urethane tube having an inner diameter of 0.099 inch and a wall thickness of 0.014 inch, and the urethane tube is heated and pulled to shrink it onto the assembly. The original, straight mandrel is removed, and a curve is established for the introducing catheter by placing it onto a curved mandrel. The catheter is then baked to set the curve, after which it is cooled and the mandrel removed. The luer 22 is attached, and bands 16 are placed on the outside of the shaft 12. The introducing catheter 10 is approximately 23.2 cm in usable length (i.e. length distal to the luer fitting 22). It is desirable for the usable length to be at least 18 cm for accessing a fallopian tube. This minimum length enables the distal tip 14 of the introducing catheter 10 to be placed close to the entrance E of the fallopian tube F, without requiring the luer fitting 22 to be inserted into the vagina V.

It is also desirable for the introducing catheter 10 to be provided with visually perceptible ink bands 16 commencing with distal band 18 approximately six cm from the distal tip 14. One of the bands 16 is aligned by a physician with the opening 0 of the cervix C to determine easily the exact depth to which the distal tip 14 is inserted within the uterus U. The bands 16 are approximately one mm in width and are spaced one cm apart, culminating in proximal band 20. Permanent indelible ink is placed directly in the exterior of the shaft 12 to form the bands. Their use is described below in more detail.

Before insertion of the introducing catheter 10, a self-sealing device 23 such as a Tuohy-Borst type of adapter or a device such as the type disclosed in U.S. Pat. No. 4,424,833 (Spector) is attached to the proximal luer 22. The sealing device 23 enables an access catheter according to the invention to be inserted through it and manipulated while maintaining a seal to prevent the escape of liquids. Preferably, the seal is maintained by a gasket which holds the access catheter in position after advancement through the introducing catheter 10. The luer 22 and the sealing device 23 have a total length of approximately 7.2 cm.

The obturator 30, FIG. 2, consists of a malleable steel rod 32, shown in dotted lines, approximately 0.030 inch in diameter and coated with polypropylene 34. The polypropylene coating 34 adds to the volume occupied by the rod 32 within the lumen of the introducing catheter 10 without increasing the stiffness of the obturator 30. The obturator 30 has a usable length of 30.3 cm, a total diameter of 0.065 inch, and assists insertion of the introducing catheter 10 by stiffening it. [1] A luer fitting 36 serves as a handle and as a stop to limit insertion within the introducing catheter 10.

[1] This allows the doctor to form the end of the introducing catheter into any desired curve to allow for anatomical variances.

An access catheter according to the invention is comprised of two sections, a main shaft and a distal segment which can have both high flexibility and high hoop strength to resist collapse. The access catheter 40, FIG. 3, is formed of a main shaft 42 having an outer diameter of 0.057 inch (1.45 mm), and a length of 31.2 cm, and a reinforced distal segment 44 with an 0.042 inch (1.07 mm) outer diameter, and a length of approximately 8 to 9 cm. The outer diameter of the shaft 42 enables it to pass freely through the introducing catheter 10, and the outer diameter of the distal segment 44 enables it to pass through a fallopian tube as described in more detail below. The shaft 42 has an inner diameter of 0.041 inch (1.04 mm) and the segment 44 has an inner diameter of 0.031 inch (0.79 mm). Approximately six cm of the distal segment 44 projects beyond the distal tip 14 of the introducing catheter 10 when the access catheter 40 is fully inserted within the introducing catheter 10. Insertion is limited by luer 45 which serves as a stop. The details of construction of the distal segment 44 are described below.

The alignment bands 46 on the proximal portion of the shaft 42 are similar in composition and spacing to the bands 16 of the introducing catheter 10. The use of the bands is described below.

It is desirable to use a guide 50, FIG. 5, during insertion of the access catheter 40 to provide extra pushability and trackability through the fallopian tube. As described above, the guide 50 is insertable through the lumen of the access catheter 40 to increase its column strength which is useful for advancing the access catheter 40 through the collapsed, narrow-diameter isthmus I of the fallopian tube F. Additionally, the entrance E may be more easily located using the flexible spring tip 52 of the guide 50, after which the access catheter 40 can be advanced along the guide 50 through the entrance E and into the fallopian tube F.

The guide 50 has a spring tip 52 approximately 6 cm in length and a main shaft 54 formed of a solid wire 0.016 inch in diameter. Preferably, the wire 54 is coated with low friction Teflon to a thickness of 0.0003 to 0.0005 inch, to establish the total outer diameter less than or equal to 0.017 inch. The guide 50 has a useful overall length of 49.2 cm. Visually perceptible bands 56 are provided on a proximal segment 57. Distal band 58 is 40.9 cm from the distal end 55 of the guide 50.

The segment 57 is formed of a sleeve placed over the Teflon coated wire 54 to provide a more suitable substrate for the bands 56 than would be provided by the Teflon surface of the wire 54. An acceptable material for the segment 57 is "K resin" (styrene butadiene) which readily accepts permanent ink. The segment 57 is approximately 8 cm in length and has an outer diameter of 0.026 inch. A luer 59 serves as a stop to limit insertion through the access catheter 40. Further, the luer 59 serves as a handle and as a visual aid for the physician to readily locate and manipulate the proximal end of the guide 50. Additionally, the luer 59 assists securing the sleeve 57 in position on the wire 54.

The small diameter and great flexibility of the guide minimizes risk of puncture of the fallopian tube. Unlike an artery which is substantially round, the fallopian tube normally is in a collapsed condition which renders insertion difficult. The combination of a guide, an access catheter, and a transfer catheter provides a substantial advantage over the conventional practice of using only a transfer catheter within the fallopian tube.

The transfer catheter 60, FIG. 4, is a single lumen catheter and has a usable length of approximately 43.3 cm. The transfer catheter 60 extends approximately one cm beyond the distal end of the access catheter when fully inserted into the access catheter 40. The transfer catheter 60 therefore can be inserted a maximum of 7 cm into the fallopian tube, as described in more detail below.

The inner and outer diameters of the transfer catheter 60 are selected based on several considerations. The minimum inner diameter is approximately 0.014 inch (0.36 mm) to accommodate a zygote. The outer diameter is approximately 0.027 inch (0.66 mm) so that the walls can be thick enough to provide sufficient stiffness (column strength) for pushability.

The transfer catheter 60 has a shaft 61 formed of an inert material such as ethylene tetrafluroethylene (ETFE), available from DuPont, which is compatible with the reproductive cells. ETFE is desirable because it can be sterilized using gamma radiation. A support sleeve 62 is formed of high density polyethylene (HDPE) to provide a strain relief section which assists transition to the luer 64. The sleeve 62 is approximately 1.0 cm in length, and has an outer diameter of 0.040 inch. The luer 64 accepts the distal end of a syringe for discharging reproductive cells when the distal tip 66 is at a desired location, as described in more detail below.

The coaxial catheter system is used as follows for depositing reproductive material into a fallopian tube. The introducing catheter 10 is inserted into the vagina V, FIG. 6, through the cervix C and into the uterus U with the assistance of the obturator 30. It is desirable to place the distal tip 14 of the introducing catheter 10 at the entrance E to the fallopian tube F. The physician determines beforehand the depth to which the introducing catheter 10 must be inserted by "sounding" the uterus to determine the actual length for the particular patient. One of the bands 16 is selected by the physician for alignment with the external opening 0 of the cervix C. A short-length sleeve 21, shown in phantom in FIG. 1, may be placed around the exterior of the shaft 12 to serve as a removable stop and to designate the selected band. The slidable sleeve 21 has an outer diameter of 0.375 inch and an inner diameter of approximately 0.104 inch which fits snugly over the shaft 12. It is desirable for at least one of the bands 16 to be positioned between 7 to 10 cm, and most preferably a band is located at 9 cm from the distal tip 14. The illustrated introducing catheter 10 has bands located between 6 to 11 cm from the distal tip 14 to accomodate a wide variety of patients.

After the obturator 30 is removed and the introducing catheter 10 is in position within the uterus, the access catheter 40 is advanced through the introducing catheter 10 and through the isthmus I of the fallopian tube F. The bands 46 of the access catheter 40 are aligned by the physician with the sealing device 23 of the introducing catheter 10. When the distal band 48 is aligned with the sealing device 23, the distal tip 49 is flush with the distal tip 14 of the introducing catheter 10. The distal band 48 is disposed approximately 30.2 cm from the distal tip 49; it is desirable to have one or more of the bands disposed between 28 to 30 cm from the distal tip 49. The distal tip 49 is insertable a maximum of six cm beyond the distal tip 14 of the introducing catheter 10 and into the fallopian tube F, which is a sufficient depth to enable the transfer catheter to be inserted well beyond the isthmus I of the tube F, as described in more detail below. The sealing device 23 is then tightened to secure the access catheter 40 in position.

When the guide 50 is used to assist insertion of the access catheter 40 into the fallopian tube F, the guide 50 is preloaded into the access catheter 40 and the combination is then inserted through the introducing catheter 10. According to his discretion, the physician can either advance the guide 50 alone through the entrance E, and then subsequently advance the access catheter 40 into the isthmus I, or the physician can advance together the combination of the guide and the outer catheter. The distal band 58 is disposed approximately 40.9 cm from the distal tip 55 of the guide 50. Preferably, at least one band is located between 38 to 48 cm from the distal tip 55.

The transfer catheter 60 is loaded according to a conventional procedure for transfer catheters in which semen and an egg are alternately introduced, separated by an air bubble, as described for example in *In Vitro Fertilization*, Jones, Jr. et al., editors, published in 1986 by Williams and Wilkins. A 20 microliter plug of growth media such as Hams Solution is drawn through the distal end 56 of the transfer catheter 50. A 20 microliter air bubble then is drawn, followed by alternating 30 microliter plugs of media containing reproductive cells and 20 microliter air bubbles. Twenty microliters of air separates the distal most plug of media containing reproductive cells from the distal end 66. In a zygote intrafallopian transfer procedure, one or more zygotes separated by air bubbles are loaded into the distal end of the transfer catheter. In either transfer procedure, the load is discharged using a minimum amount of a culture medium, e.g. less than 100 microliters, delivered through a syringe mated to the luer 64 of the transfer catheter 60.

After it is distally loaded, the transfer catheter 60 is advanced through the access catheter 40 into the fallopian tube F. The depth of insertion is determined by the physician. A fallopian tube typically has a total length of approximately 10-11 cm, and it is considered desirable by some physicians to deliver the gametes or zygotes at least half way along the length of the tube to more closely simulate natural fertilization. Visually perceptible markers may be provided on the shaft 61 of the transfer catheter; in the illustrated embodiment, the sleeve 62 and the luer 64 provide a reference relative to the proximal end of the access catheter 40 for estimating the depth of insertion.

Figure 7:
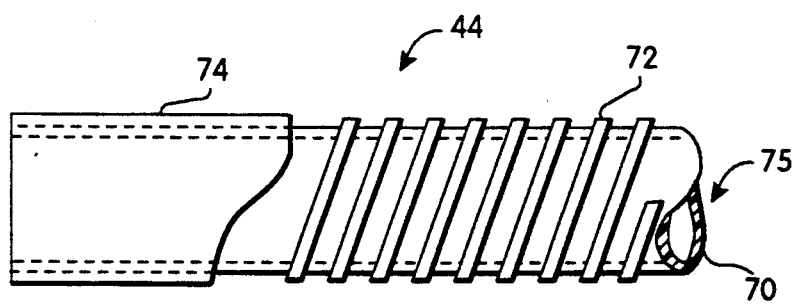
FIG. 7 is an enlarged, fragmented, section illustration of a portion of the distal segment of the access catheter of FIG. 3.

The details for the construction of the access catheter 40 are as follows. The distal segment 44 of the access catheter, 40 is a laminate construction including a polymeric liner 70, FIG. 7 a stainless steel ribbon wire spring 72 and a polymeric sleeve 74. The ribbon wire 72 serves as a reinforcing material to resist constriction of the passage 75 which communicates with a distal opening 77. An additional advantage of the stainless steel is that it is opaque to ultrasound which may be used to monitor an access procedure. Alternatively, the reinforcing material is a radiopaque material such as platinum.

The object of the laminated construction is to provide a large inner diameter (0.031 inch) lumen to accept the transfer catheter with some tolerance, and to provide a small outer diameter of approximately 0.040 inch to enable passage through the fallopian tube. This object is achieved in the illustrative embodiment using a laminate construction of two tubes which are alternately expanded and compressed, as described in more detail below, to provide exceedingly thin walls. It is desirable for the distal segment 44 to be less than 0.080 inch in diameter, and preferably less than 0.050 inch, to minimize trauma to the fallopian tube. A desirable polymeric material for the liner 70 and the sleeve 74 should have the ability to be made thin while retaining sufficient strength. An acceptable Surlyn is grade no. 9950 available from DuPont a known thermoplastic ionomer.

The distal segment 44 is formed by a series of lamination steps designed to form the walls of the segment 44 as thin as possible. A thin polymeric tube having an inner diameter of 0.020 inch and an outer diameter of 0.027 inch is provided, typically formed by extrusion, and then irradiated with an electron beam to cross-link the material. A nine cm length of the polymeric tube is then inserted inside a stainless steel hypotube or other hollow mandrel having an inner diameter of approximately 0.050 inch. One end of the polymeric tube is plugged and the other end is connected to a source of pressurized gas. The assembly is then heated and the polymeric tube inflated to stretch it radially. The assembly is placed in a cold water bath while inflated to set the desired diameter. The polymeric tube then is placed over a Teflon- coated mandrel having an outer diameter of 0.31–0.32 inch. Alligator clips are placed on either end of the polymeric tube to clamp it and avoid shrinkage in length. The polymeric tube is then heated with hot air to shrink it radially against the mandrel. A wall thickness of approximately 0.001 inch is obtained for the liner 70, which is thinner than that capable of being formed by extrusion. The alligator clips then are removed from the polymeric tube and the material damaged by the teeth of the clips is cut off.

The spring 72 is preformed using 0.001 by 0.005 inch ribbon wire, which is wound to have an inner diameter of 0.036 inch, a length of nine cm, and a coil spacing of approximately 0.004 inch. It is preferable for the ribbon wire to have a width at least twice as great as its height; and in this construction, the width is five times as great as the height which provides sufficient reinforcement while minimizing the overall thickness of the spring 72. Some space is desired between the coils to provide flexibility and, on the other hand, a close coil spacing is desired to increase resistance to collapse. A close coil spacing ensures a steeper angle of the coils which in turn reduces the tendency of the spring 72 to shift and collapse. The spring 72 then is twisted onto the polymeric liner 70 and aligned lengthwise with it. The ends of the spring 72 are grasped and manually rotated to twist the spring and snug it against the liner 70. A cyanacrylate adhesive such as Loctite is applied on each end of the spring 72 to hold it in place while the outer polymeric sleeve 74 is slid over it.

The polymeric sleeve 74 is pretreated before sliding it over the spring by expanding it within the hypotube in a manner similar to the treatment of the polymeric liner 70. After it is expanded, the sleeve 74 is slid over the liner 70 and spring 72 and secured in place with alligator clips which prevents shrinkage in length. The assembly is heated with hot air to shrink the sleeve 74 against the spring 72, as described in more detail below. The assembly is cooled and the clips are removed. A Teflon shrink tube is then placed over the assembly and heated to compress the polymeric sleeve 74 against the spring 72 and the liner 70. The inner mandrel resists further compression, and the combination of the inner resistance supported by the mandrel and the radial compression provided by the Teflon sleeve further laminates together the sleeve 74, the spring 72, and the liner 70. The Teflon sleeve is slit to remove it.

Figure 8:
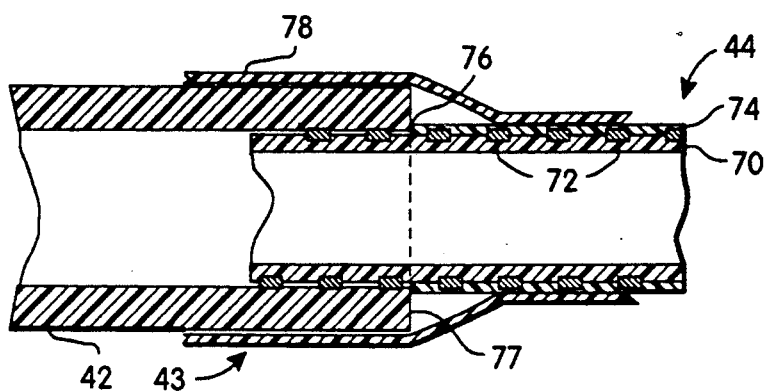
FIG. 8 is an enlarged, partial, cross-sectional view of the junction of the distal segment and the main shaft of the access catheter.

Preferably, the proximal end of the distal segment 44 is attached to the main shaft 42 by inserting approximately 4 mm of the liner 70 and the spring 72 inside the main shaft 42 as shown in FIG. 8. The proximal end 76 of the sleeve 74 terminates approximately 4 mm from the proximal end of the liner 70 and it is brought to bear against the distal end 77 of the shaft 42. A short segment 78, e.g. 6 mm in length, is centered over the junction 43. A Teflon sleeve (not shown) is added to provide radial compression and then is removed. The heating of the junction 43 of the shaft 42 and distal segment 44 provides a smooth transition without a discernable bond line. The above joining technique is particularly effective when the shaft 42 is formed of high density polyethylene grade no. LR732 available from DuPont.

From the foregoing, it will be appreciated that the invention provides a novel access catheter for accessing a female reproductive system, and an improved catheter system and method which enables accurate placement of reproductive cells within the fallopian tube. Artificial insemination is thereby accomplished without surgery and with the ability to measure exactly the depth at which the reproductive cells are deposited. The access catheter, catheter system, and method according to the invention also enable placement in the uterus or either fallopian tube of a female patient with relatively low trauma to the patient. More broadly, the access catheter and catheter system can be used to access body cavities other than those of the human female reproductive system.

Although specific features of the invention are shown in some drawings and not in others, it is for convenience only as each feature may be combined with any or all of the other features in accordance with the invention.

It should be understood, however, that the foregoing description of the invention is intended merely to be illustrative thereof and that other modifications, embodiments, and equivalents may be apparent to those skilled in the art without departing from its spirit.

Having thus described the invention what we desire to claim and secure by Letters Patent is:

1. A kit containing catheters for depositing material within the reproductive system of the female, the kit comprising:
   an introducing catheter defining a introducing lumen and having a proximal end and a distal end;
   an access catheter including:
   a shaft defining a second lumen, having a proximal end and a distal end, and having an outer diameter smaller than the diameter of said introducing lumen;

a nonexpansible segment having a proximal end and a distal end, said proximal end connected at a junction to said distal end of said shaft, said segment defining a passage communicating with said lumen at said junction and communicating with a distal opening at said distal end of said segment, and said segment being formed of at least first and second layers of material and having an outer diameter smaller than that of said shaft; and reinforcing material disposed between said first and second layers of said segment to resist constriction of said passage; and a transfer catheter having a length at least as long as that of said access catheter and having a diameter smaller than that of said second lumen of said access catheter.

2. A catheter system for accessing a portion of the reproductive system of a female, the system comprising:

an access catheter including:

a shaft defining a lumen, the shaft having a proximal end and a distal end;

a nonexpansible segment having a proximal end and a distal end, said proximal end connected at a junction to said distal end of said shaft, and said segment defining a passage communicating with said lumen at said junction and communicating with a distal opening at said distal end of said segment; and reinforcing material disposed within said segment to resist constriction of said passage; and a transfer catheter having an elongated shaft insertable through said access catheter for delivering reproductive cells carried by the transfer catheter into a desired location within the reproductive system.

3. A catheter system for accessing a portion of the female reproductive system, the system comprising:

an introducing catheter defining a first lumen and having a proximal end and a distal end; and an access catheter including:

a shaft defining a second lumen, having a proximal end and a distal end, and having an outer diameter smaller than the diameter of said first lumen;

a distal tube having a proximal end and a distal end, said proximal end connected at a junction to said distal end of said shaft, and said tube defining a passage communicating with said lumen at said junction and communicating with a distal opening at said distal end of said tube; and reinforcing material disposed within said tube to resist constriction of said passage.

4. The catheter system of claim 3 in which said access catheter includes a stop which limits insertion of said access catheter through the proximal end of said introducing catheter, said junction remaining proximal to the distal end of said introducing catheter when said access catheter is fully inserted therein.

5. The catheter system of claim 3 in which said access catheter includes at least one visually perceptible marker disposed between 28 to 38 cm from said distal end of said access catheter for alignment relative to said proximal end of said introducing catheter.

6. The catheter system of claim 3 in which said introducing catheter includes a slidable sleeve disposed about a portion of its outer surface for alignment relative to a portion of the anatomy of a patient.

7. The catheter system of claim 3 in which said introducing catheter includes at least one visually perceptible marker disposed between 6 to 11 cm from said distal end of said introducing catheter.

8. The catheter system of claim 3 further including a transfer catheter having a length at least as long as that of said access catheter and having a diameter smaller than that of said second lumen of said access catheter.

9. The catheter system of claim 8 in which said transfer catheter includes a stop for limiting insertion of said transfer catheter through said access catheter.

10. The catheter system of claim 9 in which a distal end of said transfer catheter projects slightly beyond the distal end of said access catheter when said transfer catheter is fully inserted therein.

11. The catheter system of claim 3 further including a flexible guide insertable through said access catheter to assist advancement of said access catheter into said body cavity.

12. The catheter system of claim 11 in which said guide includes at least one visually perceptible marker disposed between 38 to 48 cm from a distal end of said guide for alignment relative to said proximal end of said access catheter.

13. The catheter system of claim 12 in which said guide includes a main shaft formed of a wire which is connected at a distal end to a flexible section.

14. The catheter system of claim 13 in which said flexible section includes a coil spring.

15. The catheter system of claim 13 in which said guide includes an outer sleeve disposed about the proximal end of said shaft wire for carrying said visually perceptible marker.

* * * * *